United States Patent [19]

Kawamura et al.

[11] Patent Number: 4,849,011

[45] Date of Patent: Jul. 18, 1989

[54] 4-SUBSTITUTED-2,6-DIPHENYLPYRIDINE COMPOUNDS AND HERBICIDE CONTAINING THE SAME AS AN ACTIVE INGREDIENT

[75] Inventors: Shinichi Kawamura, Osaka; Yuzuru Sanemitsu, Ashiya; Tatsuhiro Hamada, Amagasaki; Ryo Yoshida, Kawanishi, all of Japan

[73] Assignee: Sumitomo Chemical Company, Ltd., Osaka, Japan

[21] Appl. No.: 86,397

[22] Filed: Aug. 17, 1987

[30] Foreign Application Priority Data

Sep. 16, 1986 [JP] Japan ................................ 61-218530
Feb. 26, 1987 [JP] Japan ................................ 62-44618

[51] Int. Cl.$^4$ .................... A01N 43/40; C07D 213/02
[52] U.S. Cl. ........................................ 71/94; 546/290; 546/303
[58] Field of Search ................. 546/290, 303; 568/42, 568/43; 71/94

[56] References Cited

U.S. PATENT DOCUMENTS 4,174,209 11/1974 Taylor et al. .......................... 71/94
4,451,659 5/1984 Potts ...................................... 549/4

FOREIGN PATENT DOCUMENTS 0006359 1/1980 European Pat. Off. ............ 546/290

OTHER PUBLICATIONS

Potts et al., JACS, vol. 103, pp. 3585-3586, (1981).
Chemical Abstracts, vol. 93(1), Abstract No. 8143q, (1980).
Lowry et al., An Introduction to Organic Chemistry, 1940, p. 217.
Solomons, Organic Chemistry, 2nd Edition, 1980, p. 669.
Chemical Abstracts vol. 67, No. 21, 99364q (1967).
Chemical Abstracts, vol. 93, No. 21, 19923z, (1980).
J. Am. Chem. Soc. 103 3584-3586 (1981), (2 articles) Potts, Cipullo, Ralli & Theodoridis.
J. Am. Chem. Soc. 90, 1569-1582 (1968) Beak, Bonham, Lee, Jr.
The Journal of Organic Chem., Jul. 30, 1982, Potts, Cippulo, Ralli & Theodoridis, vol. 47, No. 16, pp. 3027-3038.

Primary Examiner—Mary C. Lee
Assistant Examiner—Zinna Northington
Attorney, Agent, or Firm—Oliff & Berridge

[57] ABSTRACT

Provided herein is a comound of the formula:

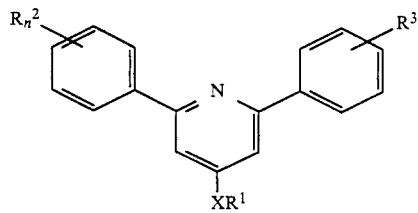

wherein $R^1$ is a $C_1$-$C_2$ alkyl group; $R^2$ is a hydrogen atom, halogen atom, methyl group, or trifluoromethyl group at the o- or m-position; $R^3$ is a halogen atom, methyl group, or trifluoromethyl group; and X is an oxygen or sulfur atom. It has an outstanding herbicidal effect and selectivity for crop plants and weeds. It is useful as a herbicide.

7 Claims, No Drawings

4-SUBSTITUTED-2,6-DIPHENYLPYRIDINE COMPOUNDS AND HERBICIDE CONTAINING THE SAME AS AN ACTIVE INGREDIENT

BACKGROUND OF THE INVENTION

1. Field of the Invention

The present invention relates to a new 4-substituted-2,6-diphenylpyridine compound, a process for producing the same, and a herbicide containing the same as an active ingredient.

2. Description of the Prior Art

Heretofore, 4-substituted-2,6-diphenylpyridine compounds such as 2,6-bisphenyl-4-(methylthio)pyridine, 2,6-bis-(4'-methoxyphenyl)-4-(methylthio)pyridine, and 2,6-bis-(4'-bromophenyl)-4-(methylthio)pyridine have been described in J. Amer. Chem. Soc., 103 (12) 3585 (1981) and others. Also, 2,6-bisphenyl-4-methoxypyridine has been described in J. Amer. Chem. Soc., 90 (6) 1569 (1968). However, these publications fail to describe the biological activities of these compounds. Needless to say, they also fail to describe the chemical structure and biological activities of the 4-substituted-2,6-diphenylpyridine compound in accordance with the present invention.

SUMMARY OF THE INVENTION

In an attempt to develop a new herbicide, the present inventors carried out a series of researches which led to the finding that a 4-substituted-2,6-diphenylpyridine compound represented by the general formula [I] has an outstanding herbicidal activity with good selectivity for crop plants and weeds.

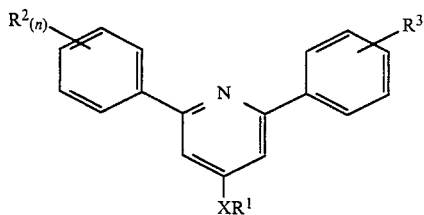

(wherein $R^1$ is a $C_1$-$C_2$ alkyl group; $R^2$ is a, halogen atom, methyl group, or trifluoromethyl group at the o- or m-position; $R^3$ is a halogen atom, methyl group, or trifluoromethyl group at the o- m- or p-position; X is an oxygen atom and n is equal to 0 or 1 or sulfur atom.)

In accordance with the present invention, a compound represented by the general formula [I] above, a process for producing the same, and a herbicide containing the same as an active ingredient are provided.

Preferable among the compounds of the invention represented by the general formula [I] above are those in which $R^1$ is a $C_1$-$C_2$ alkyl group n is 1, $R^2$ is a halogen atom or trifluoromethyl group at the m-position, and $R^3$ is a halogen atom or trifluoromethyl group at the p-position. More preferable are those compounds in which $R^1$ is a methyl group, X is a sulfur atom and $R^2$ and/or $R^3$ is a trifluoromethyl group.

Among the compounds of the invention, those in which X is a sulfur atom can be obtained by the following steps. First, an α-oxoketenedithioacetal compound represented by the general formula [II]

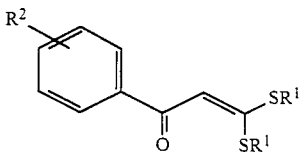

(wherein $R^1$ and $R^2$ are as defined above.) is reacted in the presence of a base with an acetophenone compound represented by the general formula [III]

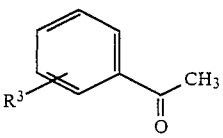

(wherein $R^3$ is as defined above.) to give a compound represented by the general formula [IV]

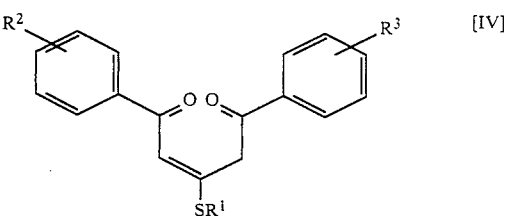

(wherein $R^1$, $R^2$, and $R^3$ are as defined above.) Subsequently, the thus obtained compound is reacted with an ammonium salt or ammonia.

The first reaction is usually performed in a solvent at a reaction temperature of 0°–50° C. for 0.5–10 hours. The reactants are in a ratio of 0.9–1.1 equivalents of acetophenone compound [III] and 2–3 equivalents of base for 1 equivalent of α-oxoketenedithioacetal compound [II].

Suitable solvents for the reaction include ethers such as diethyl ether, diisopropyl ether, dioxane, tetrahydrofuran, diethyleneglycol dimethyl ether, and N,N-dimethylformamide and dimethyl sulfoxide.

Suitable base include potassium t-butoxide and sodium hydride.

The second reaction is usually performed in a solvent at a reaction temperature of 0°–130° C. for 0.5–8 hours. The reactants are used in a ratio of 1–20 equivalents, preferably 5–10 equivalents of ammonium salt or ammonia for 1 equivalent of α-oxoketenedithioacetal compound [II]. Suitable ammonium salt include ammonium acetate and ammonium chloride.

Suitable solvents for the second reaction include ethers such as diethyl ether, diisopropyl ether, dioxane, tetrahydrofuran, and diethylene glycol dimethyl ether; fatty acids such as formic acid and acetic acid; alcohols such as methanol, ethanol, isopropanol, t-butanol, octanol, cyclohexanol, methyl cellosolve, diethylene glycol, and glycerin; acid amides such as formamide, N,N-dimethylformamide, and acetamide; sulfur compounds such as dimethylsulfoxide and sulfolane; and mixtures thereof. Preferable are fatty acids and alcohols.

The above-mentioned reactions may be performed in the same reaction vessel without separation of the compound represented by the general formula [IV]. In such a case it is preferable to use tetrahydrofuran of N,N-dimethylformamide as a solvent.

Each of the reaction liquids in the first and second reactions undergoes normal treatment such as extraction with an organic solvent and condensation, and, if necessary, is purified by chromatography or recrystallization, to yield the desired compound of the invention.

Among the compounds of the invention, those in which X is a sulfur atom may also be produced in the same manner as above from an acetophenone compound represented by the general formula [V]

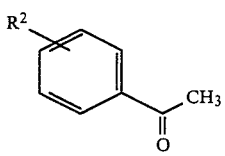

(wherein $R^2$ is as defined above.) and an α-oxoketenedithioacetal compound represented by the general formula [VI]

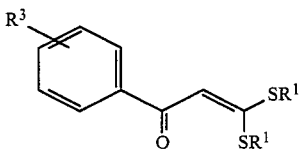

(wherein $R^1$ and $R^3$ are as defined above.)

In the production process, the α-oxoketenedithioacetal compound of formula [II] or [VI] is prepared by the reaction of the acetophenone compound of formula [V] or [III] with carbon disulfide in the presence of a base and then the reaction of thus obtained product with an alkyl halide of formula [VII]

$R^1X$          [VII]

(wherein $R^1$ is as defined above, and X denotes an iodine atom, bromine atom, or chlorine atom.) Incidentally, in the case where $R^1$ is a methyl group, the alkyl halide [VII] may be replaced by dimethyl sulfate.

This reaction is usually performed in a solvent at a reaction temperature of 0°–100° C., preferably 0°–40° C., for 0.5–10 hours, preferably 2–5 hours. The reactants are in a ratio of 0.9–1.1 equivalent of carbon disulfide, 2–2.5 equivalents of base, and 2–2.5 equivalents of alkyl halide for 1 equivalent of acetophenone compound.

The solvent includes ethers such as diethyl ether, diisopropyl ether, dioxane, tetrahydrofuran, diethyleneglycol dimethyl ether, acid amides such as N,N-dimethylformamide, sulfur compounds such as dimethyl sulfoxide and sulfolane, and their mixtures.

The reaction mixture undergoes normal treatment such as collection of crystals by filtration, extraction with an organic solvent, and condensation, and, if necessary, is purified by chromatography or recrystallization, to yield the desired α-oxoketenedithioacetal compound.

Among the compounds of the invention, the one in which X is an oxygen atom can be obtained by the following steps. First, a compound represented by the general formula [VIII]

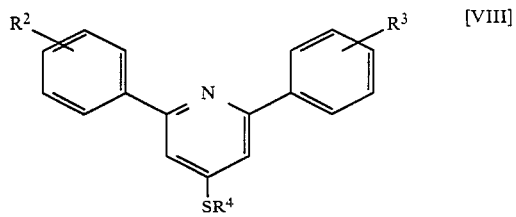

(wherein $R^2$ and $R^3$ are as defined above, and $R^4$ is a $C_1$-$C_2$ alkyl group is treated.) with an oxidizing agent to give a compound represented by the general formula [IX]

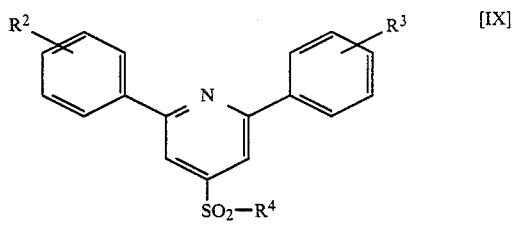

(wherein $R^2$, $R^3$, and $R^4$ are as defined above.) Subsequently, the thus obtained compound is reacted with a metal alkoxide compound represented by the general formula [X]

$R^1OM$          [X]

(wherein $R^1$ is as defined above, and M is an alkali metal.)

The first reaction is usually performed in a solvent at a reaction temperature of 0°–130° C. for 0.5–10 hours. The reactants are in a ratio of 2–5 equivalents of oxidizing agent for 1 equivalent of the compound represented by the general formula [VIII].

The solvent for the reaction includes aliphatic hydrocarbons such as hexane, heptane, ligroin, and petroleum ether; aromatic hydrocarbons such as benzene, toluene, and xylene; halogenated hydrocarbons such as chloroform, carbon tetrachloride, dichloroethane, chlorobenzene, and dichlorobenzene; ethers such as diethyl ether, diisopropyl ether, dioxane, tetrahydrofuran, and diethylene glycol dimethyl ether; ketones such as acetone; alchols such as methanol and ethanol; water; and mixtures thereof.

The oxidizing agent includes metachloroperbenzoic acid and hydrogen peroxide.

The reaction mixture undergoes normal treatment such as extraction with an organic solvent and condensation, and, if necessary, is purified by chromatography or recrystallization, to yield the desired compound of the invention.

The second reaction is usually performed in a solvent at a reaction temperature of 0°–120° C. for 0.5–10 hours. The reactants are used in a ratio of 1–10 equivalents of the metal alkoxide compound [X] for 1 equivalent of the compound represented by the formula [IX].

The solvent for the reaction includes aliphatic hydrocarbons such as hexane, heptane, ligroin, and petroleum ether; aromatic hydrocarbons such as benzene, toluene, and xylene; ethers such as diethyl ether, diisopropyl ether, dioxane, tetrahydrofuran, and diethylene glycol dimethyl ether; alcohols such as methanol, ethanol, isopropanol, t-butanol; nitriles such as acetonitrile and isobutyronitrile; tertiary amine such as pyridine, triethylamine, N,N-diethylaniline, tributylamine, and N-methylmorpholine; acid amides such as formamide, N,N-dimethylformamide, and acetamide; and sulfur compounds such as dimethyl sulfoxide and sulfolane; and mixtures thereof.

The compound of the invention has an outstanding herbicidal effect with a superior selectivity for crop plants and weeds. In other words, it is effective against the following weeds which are troublesome in the case of foliage treatment and soil treatment, and yet it does not cause phytotoxicity to major crop plants such as wheat and barley. Broad-leaved weeds such as common chickweed (*Stellaria media*), radish (*Raphanus sativus*), wild mustard (*Sinapis arvensis*), velvetleaf (*Abutilon theophrasti*), prickly sida (*Sida spinosa*), field pansy (*Viola arvensis*), cleavers (*Galium aparine*), morning glories (Ipomoea spp.), black nightshade (*Solanum nigrum*), and persian speedwell (*Veronica persica*). Gramineous weeds such as Japanese millet (*Echinochloa frumentacea*), barnyard grass (*Echinochloa crusgalli*), green foxtail (*Setaria viridis*), large crab-grass (*Digitaria sanguinalis*), oats (*Avena sativa*), and wild oats (*Avena fatua*).

The compound of the invention has a herbicidal effect on gramineous weeds such as barnyard grass (*Echinochloa oryzoides*) which are troublesome in flooded paddy fields, and yet it does not cause any substantial chemical injury to rice.

For use as an active ingredient of a herbicide, the compound of the invention is formulated into an emulsifiable concentrate, wettable powder, suspension, or granule by mixing with solid carriers, liquid carriers, surface active agents, or other adjuvants.

The formulations contain the compound of the invention in an amount of 1-90 wt%, preferably 2-80 wt%.

Solid carriers include fine powder and granular materials such as kaolin clay, attapulgite clay, bentonite, Japanese acid clay, pyrophyllite, talc, diatomaceous earth, calcite, walnut powder, urea, ammonium sulfate, and synthetic hydrated silicon oxide. Liquid carriers include aromatic hydrocarbons such as xylene and methyl naphthalene; alcohols such as isopropanol, ethylene glycol, and cellosolve; ketones such as acetone, cyclohexanone, and isophorone; vegetable oils such as soybean oil and cottonseed oil; and dimethyl sulfoxide, N,N-dimethylformamide, acetonitrile, and water.

The surface active agent used for emulsification, dispersion, and spreading include anionic surface active agents such as alkylsulfate, alkylsulfonate, alkylarylsulfonate, dialkylsulfosuccinate, and polyoxyethylene alkylaryl ether phosphate; and nonionic surface active agents such as polyoxyethylene alkylether, polyoxyethylene alkylaryl ether, polyoxyethylenepolyoxypropylene block copolymer, sorbitan fatty acid ester, and polyoxyethylene sorbitan fatty acid ester.

The adjuvants for preparations include ligninsulfonate, arginate, polyvinyl alcohol, gum arabic, CMC (carboxymethyl cellulose), and PAP (isopropyl acid phosphate).

The compound of the invention, after formulation into preparations, is used for soil treatment or foliage treatment before or after the germination of weeds or for water treatment before the germination of weeds. The soil treatment includes soil surface treatment and soil incorporation treatment, and the foliage treatment may be accomplished by spraying from above the plants or by spraying in such a manner that weeds alone are treated. The compound of the invention is preferably used for foliage treatment.

The herbicide containing the compound of the invention as an active ingredient is used at a dosage of 0.1-200 g, preferably 0.5-80 g, per acre depending on weather conditions, form of preparations, time of treatment, method of treatment, place of treatment, weeds, and crop plants. A prescribed amount of emulsifiable concentrate, wettable powder, or suspension is diluted with 1-10 liters of water per acre. (If necessary, a spreader and other adjuvants may be added to the water.) Granules are applied as such without dilution.

The spreader includes polyoxyethylene resin acid (ester), ligninsulfonate, abietate, dinaphthylmethanedisulfonate, and paraffin as well as the above-mentioned surface active agents.

The compound of the invention may be used together with other herbicides to improve their activity as herbicides, and in some cases, a synergistic effect can be expected. Further, they may be applied in combination with insecticides, acaricides, fungicides, plant growth regulators, fertilizers, etc.

Furthermore, the compound of the invention can be used as a herbicide applicable to agricultural plowed fields as well as paddy fields. It is also useful as a herbicide to be employed for orchards, pasture lands, lawns, forests, non-agricultural fields, etc.

DETAILED DESCRIPTION OF THE INVENTION

The invention will be described in more detail with reference to the following production examples, formulation examples, and test examples, which are not intended to limit the scope of the invention.

Production Example 1

(Production of Compound #77 of the invention)

To 20 ml of tetrahydrofuran solution containing 0.60 g of m-chloroacetophenone was added 1.0 g of potassium t-butoxide at room temperature, followed by stirring for 30 minutes. Further, 1 g of 3,3-bis-(methylthio)-1-(4'-chlorophenyl)-2-propen-1-one was added, followed by stirring for 1 hour. Subsequently, 20 ml of acetic acid and 3 g of ammonium acetate were added, and reaction was carried out for 3 hours under reflux, while distilling away tetrahydrofuran. The reaction liquid was neutralized with an aqueous solution of sodium hydroxide, and the neutralized solution was extracted twice with 50 ml portions of ethyl acetate. The extract was dried with anhydrous magnesium sulfate. Ethyl acetate was distilled away under reduced pressure and the residues were recrystallized from isopropanol to give 1.0 g of 2-(3'-chlorophenyl)-4-methylthio-6-(4'-chlorophenyl)pyridine. (m.p. 98.4° C.)

Production Example 2

(Production of Compound #57 of the invention)

To 20 ml of tetrahydrofuran solution containing 0.64 g of m-trifluoromethylacetophenone was added 0.9 g of potassium t-butoxide at room temperature, followed by stirring for 30 minutes. Further, 1 g of 3,3-bis-(methylthio)-1-(4'-trifluoromethylphenyl)-2-propen-1-one was added, followed by stirring for 1 hour. Subsequently, 20 ml of acetic acid and 3 g of ammonium acetate were added, and reaction was carried out for 3 hours under reflux, while distilling away tetrahydrofuran. The reaction liquid was neutralized with an aqueous solution of sodium hydroxide, and the neutralized solution was extracted twice with 50 ml portion of ethyl acetate. The extract was dried with anhydrous magnesium sulfate. Ethyl acetate was distilled away under reduced pressure and the residues were recrystallized from isopropanol to give 1.4 g of 2-(3'-trifluoromethylphenyl)-4-methylthio-6-(4'-trifluoromethylphenyl)pyridine. (m.p. 98.5° C.)

Production Example 3

(Production of Compound #4 of the invention)

To 20 ml of tetrahydrofuran solution containing 0.69 g of m-chloroacetophenone was added 1.1 g of potassium t-butoxide at room temperature, followed by stirring for 30 minutes. Further, 1 g of 3,3-bis-(methylthio)-1-phenyl-2-propen-1-one was added, followed by stirring for 1 hour. Subsequently, 20 ml of acetic acid and 3 g of ammonium acetate were added, and reaction was carried out for 3 hours under reflux, while distilling away tetrahydrofuran. The reaction liquid was neutralized with an aqueous solution of sodium hydroxide, and the neutralized solution was extracted twice with 50 ml portions of ethyl acetate. The extract was dried with anhydrous magnesium sulfate. Ethyl acetate was distilled away under reduced pressure and the residues were recrystallized from isopropanol to give 1.1 g of 2-(3'-chloromethylphenyl)-4-methylthio-6-phenylpyridine. (m.p. 56.8° C.)

Production Example 4

(Production of Compound #10 of the invention)

To 20 ml of tetrahydrofuran solution containing 0.84 g of m-trifluoroacetophenone was added 1.1 g of potassium t-butoxide at room temperature, followed by stirring for 30 minutes. Further, 1 g of 3,3-bis-(methylthio)-1-phenyl-2-propen-1-one was added, followed by stirring for 1 hour. Subsequently, 20 ml of acetic acid and 3 g of ammonium acetate were added, and reaction was carried out for 3 hours under reflux, while distilling away tetrahydrofuran. The reaction liquid was neutralized with an aqueous solution of sodium hydroxide, and the neutralized solution was extracted twice with 50 ml portions of ethyl acetate. The extract was dried with anhydrous magnesium sulfate. Ethyl acetate was distilled away under reduced pressure and the residues were recrystallized from isopropanol to give 1.4 g of 2-(3'-trifluoromethylphenyl)-4-methylthio-6-phenylpyridine. (m.p. 79.1° C.)

Production Example 5

(Production of Compound #61 of the invention)

To 20 ml of chloroform solution containing 1 g of 2-(3'-trifluoromethyl-phenyl)-4-methylthio-6-(4'-trifluoromethylphenyl)pyridine (Compound #57 of the invention) was added 0.9 g of m-chlorobenzoic acid at room temperature, followed by stirring for 10 hours. To the reaction liquid was added 100 ml of chloroform, and the chloroform solution was washed with an aqueous solution of sodium thiosulfate and then with an aqueous solution of sodium hydroxide. The chloroform solution was dried with anhydrous magnesium sulfate, and chloroform was distilled away under reduced pressure. Thus there was obtained 1.05 g of white crystals.

The white crystals were dissolved in a mixture composed of 10 ml of ethanol and 10 ml of tetrahydrofuran. To the solution was added 0.3 g of sodium ethoxide, followed by refluxing for 5 hours. The solvent was distilled away under reduced pressure. 50 ml of water was added, and the solution was extracted twice with 50 ml portions of ethyl acetate. The extract was dried with anhydrous magnesium sulfate. The solvent was distilled away under reduced pressure and the residues were purified by column chromatography to give 0.85 g of 2-(3'-trifluoromethylphenyl)-4-ethoxy-6-(4'-trifluoromethylphenyl)pyridine. (m.p. 95.1° C.)

Table 1 below shows the compounds of the invention produced in accordance with the above-mentioned process.

TABLE 1

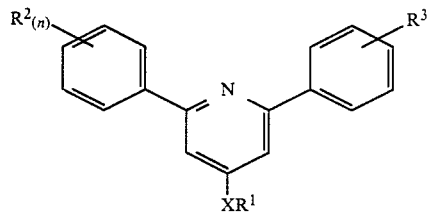

| Compound number | X | $R^1$ | n | $R^2$ | $R^3$ | Physical properties | |
|---|---|---|---|---|---|---|---|
| 1 | S | $CH_3$ | 0 | | m-F | mp | 59.5° C. |
| 2 | S | $CH_3$ | 0 | | p-F | mp | 79.2° C. |
| 3 | S | $CH_3$ | 0 | | o-Cl | mp | 110.8° C. |
| 4 | S | $CH_3$ | 0 | | m-Cl | mp | 56.8° C. |
| 5 | S | $CH_3$ | 0 | | p-Cl | mp | 81.8° C. |
| 6 | S | $CH_3$ | 0 | | o-Br | mp | 122.0° C. |
| 7 | S | $CH_3$ | 0 | | m-Br | mp | 75.0° C. |
| 8 | S | $CH_3$ | 0 | | p-Br | mp | 80.9° C. |
| 9 | S | $CH_3$ | 0 | | o-$CF_3$ | mp | 58.5° C. |
| 10 | S | $CH_3$ | 0 | | m-$CF_3$ | mp | 79.1° C. |
| 11 | S | $CH_3$ | 0 | | p-$CF_3$ | mp | 95.5° C. |
| 12 | S | $CH_3$ | 0 | | o-$CH_3$ | mp | 74.3° C. |
| 13 | S | $CH_3$ | 0 | | m-$CH_3$ | mp | 75.0° C. |
| 14 | S | $CH_3$ | 0 | | p-$CH_3$ | mp | 79.8° C. |
| 15 | O | $C_2H_5$ | 1 | m-Br | p-$CF_3$ | mp | 113.2° C. |

| Compound number | X | $R^1$ | $R^2$ | (n) | $R^3$ | Physical properties | |
|---|---|---|---|---|---|---|---|
| 16 | O | $C_2H_5$ | | 0 | o-$CH_3$ | $n_D$(25° C.) | 1.6170 |
| 17 | O | $CH_3$ | H | | m-F | mp | 64.0° C. |
| 18 | O | $C_2H_5$ | H | | m-Br | $n_D$(24° C.) | 1.6406 |
| 19 | O | $C_2H_5$ | H | | p-F | mp | 71.7° C. |
| 20 | O | $CH_3$ | H | | p-Cl | $n_D$(26° C.) | 1.6528 |
| 21 | O | $C_2H_5$ | H | | p-$CF_3$ | mp | 88.7° C. |
| 22 | O | $C_2H_5$ | o-$CH_3$ | 1 | p-Br | $n_D$(26° C.) | 1.6140 |
| 23 | O | $CH_3$ | o-$CH_3$ | 1 | p-F | $n_D$(26° C.) | 1.6135 |
| 24 | S | $CH_3$ | o-$CH_3$ | 1 | o-$CH_3$ | $n_D$(26° C.) | 1.6267 |
| 25 | S | $CH_3$ | o-$CH_3$ | 1 | m-Cl | mp | 65.2° C. |
| 26 | S | $CH_3$ | o-$CH_3$ | 1 | m-$CF_3$ | $n_D$(27° C.) | 1.5928 |
| 27 | S | $CH_3$ | o-$CH_3$ | 1 | p-F | $n_D$(24° C.) | 1.6395 |
| 28 | S | $CH_3$ | o-$CH_3$ | 1 | p-Cl | mp | 61.5° C. |
| 29 | S | $CH_3$ | o-$CH_3$ | 1 | p-Br | $n_D$(24° C.) | 1.6605 |
| 30 | S | $CH_3$ | o-$CH_3$ | 1 | p-$CF_3$ | $n_D$(24° C.) | 1.6019 |
| 31 | S | $CH_3$ | o-$CH_3$ | 1 | p-$CH_3$ | mp | 87.5° C. |
| 32 | O | $C_2H_5$ | o-$CH_3$ | 1 | p-$CF_3$ | $n_D$(24° C.) | 1.5635 |
| 33 | S | $CH_3$ | o-$CF_3$ | 1 | m-Cl | mp | 103.0° C. |
| 34 | S | $CH_3$ | o-$CF_3$ | 1 | m-$CF_3$ | mp | 96.9° C. |
| 35 | S | $CH_3$ | o-$CF_3$ | 1 | p-F | mp | 91.1° C. |
| 36 | S | $CH_3$ | o-$CF_3$ | 1 | p-Cl | mp | 128.4° C. |
| 37 | S | $CH_3$ | o-$CF_3$ | 1 | p-Br | mp | 132.4° C. |
| 38 | S | $CH_3$ | o-$CF_3$ | 1 | p-$CF_3$ | mp | 111.5° C. |
| 39 | S | $CH_3$ | o-$CF_3$ | 1 | p-$CH_3$ | mp | 115.4° C. |
| 40 | S | $CH_3$ | o-F | 1 | m-Cl | mp | 93.8° C. |
| 41 | S | $CH_3$ | o-F | 1 | p-Cl | mp | 92.8° C. |
| 42 | S | $CH_3$ | o-Cl | 1 | m-$CF_3$ | mp | 71.7° C. |
| 43 | S | $CH_3$ | o-Cl | 1 | p-Cl | mp | 120.0° C. |
| 44 | S | $CH_3$ | o-Br | 1 | m-Cl | mp | 157.3° C. |
| 45 | S | $CH_3$ | o-Br | 1 | p-Cl | mp | 122.5° C. |
| 46 | S | $CH_3$ | o-$CF_3$ | 1 | m-F | mp | 77.2° C. |
| 47 | S | $CH_3$ | o-$CF_3$ | 1 | m-Cl | mp | 99.5° C. |
| 48 | S | $CH_3$ | o-$CF_3$ | 1 | m-Br | mp | 104.6° C. |
| 49 | S | $CH_3$ | m-$CF_3$ | 1 | m-$CF_3$ | mp | 102.4° C. |
| 50 | S | $CH_3$ | m-$CF_3$ | 1 | m-$CH_3$ | mp | 61.2° C. |
| 51 | S | $CH_3$ | m-$CF_3$ | 1 | p-F | mp | 75.1° C. |

TABLE 1-continued

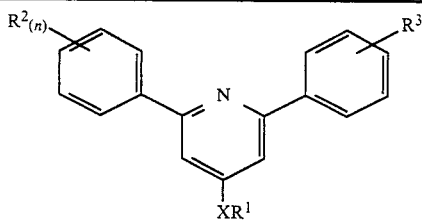

| | X | R¹ | R²(n) | R³ | | |
|---|---|---|---|---|---|---|
| 52 | S | $CH_3$ | m-$CF_3$ | 1 p-Cl | mp | 102.6° C. |
| 53 | O | $CH_3$ | m-$CF_3$ | 1 p-Cl | mp | 99.1° C. |
| 54 | O | $C_2H_5$ | m-$CF_3$ | 1 p-Cl | mp | 84.9° C. |
| 55 | O | $C_2H_5$ | m-$CF_3$ | 1 p-$CH_3$ | mp | 77.4° C. |
| 56 | S | $CH_3$ | m-$CF_3$ | 1 p-Br | mp | 112.8° C. |
| 57 | S | $CH_3$ | m-$CF_3$ | p-$CF_3$ | mp | 98.5° C. |
| 58 | S | $CH_3$ | m-$CF_3$ | p-$CH_3$ | mp | 89.6° C. |
| 59 | S | $C_2H_5$ | m-$CF_3$ | p-$CF_3$ | mp | 100.4° C. |
| 60 | O | $CH_3$ | m-$CF_3$ | p-$CF_3$ | mp | 80.1° C. |
| 61 | O | $C_2H_5$ | m-$CF_3$ | p-$CF_3$ | mp | 95.1° C. |
| 62 | O | $C_2H_5$ | m-$CF_3$ | p-Br | mp | 90.6° C. |
| 63 | O | $C_2H_5$ | m-F | p-Cl | mp | 82.6° C. |
| 64 | O | $C_2H_5$ | m-F | p-F | mp | 101.3° C. |
| 65 | S | $CH_3$ | m-F | p-F | mp | 85.0° C. |
| 66 | S | $CH_3$ | m-F | p-Cl | mp | 108.3° C. |
| 67 | S | $CH_3$ | m-F | p-Br | mp | 109.6° C. |
| 68 | S | $CH_3$ | m-F | p-I | mp | 85.3° C. |
| 69 | S | $CH_3$ | m-F | p-$CF_3$ | mp | 73.7° C. |
| 70 | S | $CH_3$ | m-F | p-$CH_3$ | mp | 81.8° C. |
| 71 | O | $C_2H_5$ | m-F | p-$CF_3$ | mp | 101.1° C. |
| 72 | O | $CH_3$ | m-F | p-Br | mp | 82.5° C. |
| 73 | S | $CH_3$ | m-Cl | m-F | mp | 86.7° C. |
| 74 | S | $CH_3$ | m-Cl | m-Cl | mp | 119.0° C. |
| 75 | S | $CH_3$ | m-Cl | m-$CH_3$ | mp | 65.6° C. |
| 76 | S | $CH_3$ | m-Cl | p-F | mp | 83.6° C. |
| 77 | S | $CH_3$ | m-Cl | p-Cl | mp | 98.4° C. |
| 78 | S | $CH_3$ | m-Cl | p-Br | mp | 96.9° C. |
| 79 | O | $C_2H_5$ | m-Cl | p-Br | mp | 111.6° C. |
| 80 | O | $CH_3$ | m-Cl | p-Br | mp | 98.6° C. |
| 81 | O | $C_2H_5$ | m-Cl | p-Cl | mp | 106.8° C. |
| 82 | S | $CH_3$ | m-Cl | p-I | mp | 109.2° C. |
| 83 | S | $CH_3$ | m-Cl | p-$CF_3$ | mp | 105.6° C. |
| 84 | O | $CH_3$ | m-Cl | p-$CF_3$ | mp | 99.8° C. |
| 85 | O | $C_2H_5$ | m-Cl | p-$CF_3$ | mp | 119.4° C. |
| 86 | S | $CH_3$ | m-Cl | P-$CH_3$ | $n_D(27°$ C.) | 1.5621 |
| 87 | O | $C_2H_5$ | m-Br | p-F | mp | 91.0° C. |
| 88 | S | $CH_3$ | m-Br | p-F | mp | 76.4° C. |
| 89 | S | $C_2H_5$ | m-Br | p-Cl | mp | 93.4° C. |
| 90 | S | $CH_3$ | m-Br | p-Br | mp | 100.4° C. |
| 91 | S | $CH_3$ | m-Br | p-I | mp | 107.7° C. |
| 92 | S | $CH_3$ | m-Br | p-$CF_3$ | mp | 119.6° C. |
| 93 | S | $CH_3$ | m-Br | p-$CH_4$ | $n_D(25°$ C.) | 1.6712 |
| 94 | O | $C_2H_5$ | m-Br | p-Cl | mp | 100.2° C. |
| 95 | O | $C_2H_5$ | m-Br | p-Br | mp | 109.5° C. |

The following examples illustrate the synthesis of α-oxoketenedithioacetal from which is produced the compound of the invention.

Production Example 6

(Synthesis of 3,3-bis-(methylthio)-1-(3'-trifluoromethylphenyl)-2-propen-1-one)

To 200 ml of N,N-dimethylformamide solution containing 20 g of 3'-trifluoromethylacetophenone and 8.0 g of carbon disulfide was added 9.2 g of sodium hydride (60%) at room temperature, followed by stirring for 30 minutes. Further, 40 g of methyl iodide was added dropwise over 30 minutes, followed by stirring for 2 hours. 500 ml of iced water was slowly added to cause crystals to separate out. The crystals were filtered out and washed with 40 ml of hexane. Upon recrystallization from isopropanol, there was obtained 27 g of 3,3-bis(methylthio)-1-(3'-trifluoromethylphenyl)-2-propen-1-one. (m.p. 89.5° C.)

Production Example 7

(Synthesis of 3,3-bis(methylthio)-1-(2'-methylphenyl)-2-propen-1-one)

To 150 ml of N,N-dimethylformamide solution containing 15 g of o-methylacetophenone and 9 g of carbon disulfide was added 10 g of sodium hydride (60% oil dispersion) at room temperature, followed by stirring for 30 minutes. Further, 40 g of methyl iodide was added dropwise over 30 minutes, followed by stirring for 2 hours. 400 ml of iced water was slowly added to cause crystals to separate out. The crystals were filtered out and washed with 40 ml of hexane. Upon recrystallization from isopropanol, there was obtained 22 g of 3,3-bis(methylthio)-1-(2'-methylphenyl)-2-propen-1-one. (m.p. 96.2° C.)

Table 2 below shows α-oxoketenedithioacetal compounds produced in accordance with above-mentioned process.

TABLE 2

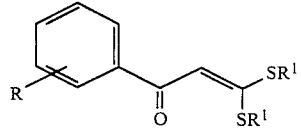

| Code of Compound | R¹ | R | Physical properties | |
|---|---|---|---|---|
| (a) | $CH_3$ | m-F | mp | 96.0° C. |
| (b) | $CH_3$ | p-F | mp | 88.7° C. |
| (c) | $CH_3$ | o-Cl | mp | 153.6° C. |
| (d) | $CH_3$ | m-Cl | mp | 66.6° C. |
| (e) | $CH_3$ | p-Cl | mp | 109.7° C. |
| (f) | $CH_3$ | o-Br | mp | 134.4° C. |
| (g) | $CH_3$ | m-Br | mp | 79.9° C. |
| (h) | $CH_3$ | p-Br | mp | 81.0° C. |
| (i) | $CH_3$ | o-$CH_3$ | mp | 96.2° C. |
| (j) | $CH_3$ | o-$CF_3$ | mp | 109.1° C. |
| (k) | $CH_3$ | m-$CF_3$ | mp | 89.5° C. |
| (l) | $CH_3$ | p-$CF_3$ | mp | 88.0° C. |

The following examples show formulations for the compound of the invention. The parenthesized number corresponds to the compound number in Table 1. Quantities are expressed in parts by weight.

Formulation Example 1

A wettable powder is prepared by thoroughly crushing and mixing 80 parts of the compound (28) or (46), 3 parts of calcium ligninsulfonate, 2 parts of sodium laurylsulfate, and 15 parts of synthetic hydrated silicon oxide.

Formulation Example 2

An emulsifiable concentrate is prepared by thoroughly mixing 10 parts of each of the compounds (1) to (96), 14 parts of polyoxyethylene styrylphenyl ether, 6 parts of calcium dodecylbenzenesulfonate, and 70 parts of xylene.

Formulation Example 3

A granule is prepared by thoroughly crushing and mixing 2 parts of the compound (52) or (56), 1 part of synthetic hydrated silicon oxide, 2 parts of calcium ligninsulfonate, 30 parts of bentonite, and 65 parts of kaolin clay, followed by mixing with water and granulation and drying.

Formulation Example 4

A suspension is prepared by mixing 25 parts of the compound (28) or (57), 3 parts of polyoxyethylenesorbitan monooleate, 3 parts of CMC, and 69 parts of water, followed by wet grinding to a particle size finer than 5 microns.

The following test examples illustrate the effectiveness of the compound of the invention as an active ingredient of a herbicide. The compounds used in the test examples are referenced by the compound number given in Table 1. The compounds used for control are referenced by the compound code given in Table 3.

The effectiveness is further given intermediate ratings of 1, 2, 3, and 4 according to the results of observation.

Test Example 1 (Foliage treatment for upland field)

Upland field soil filled in a cylindrical plastics pot (10 cm in diameter and 10 cm deep) was sown with Japanese millet, oats, radish, and velvetleaf. The plants were grown in a greenhouse for 10 days. A designed amount of the test compound formulated in an emulsifiable concentrate according to Formulation Example 2 was diluted with water containing a spreader, and the dilution was sprayed over the foliage of the test plants by means of a small sprayer at a spray volume of 10 liters per acre. After the treatment, the plants were grown in a greenhouse for 20 days and the herbicidal effect was observed. The results are shown in Table 4.

TABLE 3

| Compound Code | Structural formula | Remarks |
|---|---|---|
| (A) | $CH_3-As(=O)(ONa)(ONa)$ | DSMA (Commercial herbicide) |
| (B) | 2,4-dichlorophenoxyacetic acid ($Cl_2C_6H_3-O-CH_2CO_2H$) | 2,4-D (Commercial herbicide) |
| (C) | 3-amino-1,2,4-triazole ($NH_2$–triazole ring with N—N—H) | Amitrole (Commercial herbicide) |
| (D) | 2,6-bis(4-methoxyphenyl)-4-(methylthio)pyridine ($CH_3O$-phenyl-pyridine($SCH_3$)-phenyl-$OCH_3$) | described in J. Amer. Chem. Soc., 103, 3585 (1981) |
| (E) | 2,6-bis(4-bromophenyl)-4-(methylthio)pyridine (Br-phenyl-pyridine($SCH_3$)-phenyl-Br) | described in J. Amer. Chem. Soc., 103, 3585 (1981) |
| (F) | 2,6-diphenyl-4-methoxypyridine (phenyl-pyridine($OCH_3$)-phenyl) | described in J. Amer. Chem., Soc., 90, 1569, (1968) |

The herbicidal effect was evaluated by visually observing the germination and growth of the test plants. The effectiveness is given the lowest rating "0" when there is no substantial difference between the treated plot and the untreated plot. The effectiveness is given the highest rating "5" when the test plants in the treated plot are completely killed or hindered from growing.

TABLE 4

| Compound No. | Dosage (g/acre) | Herbicidal Activity | | | |
|---|---|---|---|---|---|
| | | Barnyardgrass | Oat | Radish | Velvetleaf |
| (1) | 20 | 5 | — | 5 | 4 |

TABLE 4-continued

| Compound No. | Dosage (g/acre) | Herbicidal Activity | | | |
|---|---|---|---|---|---|
| | | Barnyardgrass | Oat | Radish | Velvetleaf |
| (2) | 20 | — | — | 5 | 5 |
| (4) | 20 | 4 | — | 5 | 5 |
| (7) | 20 | — | — | 5 | 5 |
| | 5 | — | — | 5 | 5 |
| (8) | 20 | — | — | 5 | 5 |
| | 5 | — | — | 4 | 4 |
| (9) | 20 | 5 | — | 5 | 5 |
| | 5 | — | — | — | 5 |
| (10) | 20 | 5 | — | 5 | 5 |
| | 5 | — | — | 4 | 4 |
| (11) | 20 | — | — | 5 | 5 |
| (12) | 20 | 5 | — | 5 | 5 |
| | 5 | — | — | 5 | 5 |
| (13) | 20 | — | — | 5 | 5 |
| (15) | 20 | — | — | 5 | 5 |
| (21) | 20 | — | — | 5 | 5 |
| (25) | 80 | 4 | 4 | 5 | 5 |
| | 20 | 4 | — | 4 | 4 |
| (27) | 80 | 5 | 4 | 5 | 5 |
| | 20 | 5 | — | 5 | 5 |
| (28) | 80 | 5 | 4 | 5 | 5 |
| | 20 | 4 | — | 4 | 5 |
| (29) | 80 | 5 | 4 | 5 | 5 |
| | 20 | 4 | — | 5 | 4 |
| (30) | 80 | 5 | 4 | 5 | 5 |
| | 20 | — | — | 5 | 5 |
| (35) | 80 | 5 | 4 | 5 | 5 |
| | 20 | 5 | 4 | 5 | 5 |
| (38) | 80 | 5 | 4 | 5 | 5 |
| | 20 | 5 | — | 5 | 5 |
| (42) | 80 | 5 | 4 | 5 | 5 |
| (46) | 80 | 4 | 4 | 5 | 5 |
| (47) | 80 | 4 | 5 | 5 | 4 |
| (49) | 80 | 5 | 5 | 5 | 5 |
| | 20 | 4 | — | 5 | 5 |
| (50) | 80 | 5 | 4 | 5 | 5 |
| (51) | 80 | 5 | 4 | 5 | 5 |
| | 20 | 5 | 4 | 5 | 5 |
| (52) | 80 | 4 | 4 | 5 | 4 |
| | 20 | — | — | 5 | 4 |
| (53) | 20 | — | — | 5 | 5 |
| (54) | 20 | 4 | — | 5 | 5 |
| (56) | 80 | 4 | 4 | 4 | 5 |
| (57) | 80 | 4 | 4 | 5 | 5 |
| | 20 | 4 | — | 5 | 5 |
| (58) | 80 | 4 | 4 | 5 | 5 |
| (60) | 20 | 4 | — | 5 | 5 |
| (62) | 20 | — | — | 5 | 5 |
| (63) | 20 | — | — | 5 | 5 |
| (65) | 80 | 5 | 4 | 5 | 5 |
| (69) | 20 | — | — | 5 | 4 |
| (75) | 80 | 4 | 4 | 5 | 5 |
| (76) | 20 | — | — | 5 | 4 |
| (77) | 20 | — | — | 5 | 5 |
| (81) | 20 | — | — | 5 | 5 |
| (83) | 80 | 4 | 4 | 5 | 5 |
| (84) | 20 | — | — | 5 | 5 |
| (85) | 20 | — | — | 5 | 5 |
| (86) | 80 | 4 | 4 | 5 | 4 |
| (88) | 80 | 5 | 4 | 5 | 5 |
| | 20 | 4 | — | 5 | 5 |
| (89) | 80 | 4 | 4 | 4 | 4 |
| (90) | 80 | 4 | 4 | 4 | 5 |
| (91) | 80 | 4 | 4 | 5 | 5 |
| (93) | 80 | 4 | 4 | 4 | 5 |
| (94) | 20 | — | — | 5 | 5 |
| (95) | 20 | — | — | 5 | 5 |
| (A) | 80 | 5 | 3 | 5 | 0 |
| | 20 | 3 | 1 | — | 0 |
| (D) | 80 | 1 | 0 | 1 | 1 |
| | 20 | 0 | 0 | 0 | 0 |
| (E) | 80 | 2 | 1 | 2 | 1 |
| | 20 | 0 | 0 | 1 | 0 |

Test Example 2 (Foliage treatment for upland field)

Upland field soil filled in a vat measuring 33 by 23 cm and 11 cm deep was sown with wheat, cleavers, common chickweed, field pansy, and persian speedwell. The plants were grown in a greenhouse for 18 days. The grown plants (1-4 leaf stage and 2-12 cm long) were subjected to foliage treatment from above using a small sprayer with a diluted liquid (10 liters per are) containing a prescribed amount of sample emulsifiable concentrate prepared according to Formulation Example 2. (The diluent contains a spreader.) Twenty days after the treatment, the herbicidal effect and phytotoxicity were observed. The results are shown in Table 5.

TABLE 5

| Compound No. | Dosage (g/acre) | Herbicidal Activity | | | | |
|---|---|---|---|---|---|---|
| | | Wheat | Field pansy | Persian speedwell | Common chickweed | Cleavers |
| (1) | 10 | 1 | 5 | — | 4 | 4 |
| | 2.5 | 1 | 5 | — | 4 | — |
| (2) | 5 | 0 | 5 | 4 | 4 | — |
| | 1.25 | 0 | 4 | 4 | 4 | — |
| (4) | 10 | 1 | 5 | 5 | 5 | 4 |
| | 2.5 | 1 | 5 | 5 | 4 | — |
| (9) | 10 | 0 | 5 | 4 | 5 | — |
| | 2.5 | 0 | 4 | 4 | 5 | — |
| (10) | 10 | 1 | 5 | 5 | 5 | 4 |
| | 2.5 | 0 | 5 | 5 | 4 | 4 |
| (25) | 2.5 | 0 | 5 | 5 | 4 | 4 |
| (26) | 10 | 1 | 5 | 5 | 5 | 4 |
| (28) | 2.5 | 1 | 5 | 5 | 5 | 4 |
| | 0.63 | 0 | 5 | 5 | — | — |
| (30) | 5 | 1 | 5 | 5 | 5 | 5 |
| | 1.25 | 1 | 5 | 5 | 5 | 5 |
| (31) | 10 | 1 | 5 | 5 | 5 | 4 |
| (33) | 10 | 1 | 5 | 5 | 5 | 5 |
| (42) | 5 | 0 | 5 | 4 | 5 | — |
| (46) | 0.63 | 1 | 5 | 4 | 4 | — |
| (47) | 5 | 1 | 5 | 5 | — | 4 |
| (48) | 5 | 1 | 5 | 5 | 4 | 4 |
| (50) | 5 | 0 | 5 | 5 | 4 | 4 |
| (52) | 2.5 | 1 | 5 | 4 | 4 | 4 |
| (53) | 10 | 0 | 5 | — | 4 | 4 |
| (54) | 5 | 1 | 5 | 5 | 4 | 5 |
| | 1.25 | 0 | 5 | 4 | 4 | — |
| (56) | 2.5 | 1 | 5 | 5 | 4 | 4 |
| (57) | 2.5 | 1 | 5 | 5 | 5 | 5 |
| | 0.63 | 1 | 5 | 5 | 4 | 4 |
| (58) | 10 | 1 | 5 | 5 | 5 | 5 |
| (65) | 10 | 1 | 4 | 5 | 4 | — |
| (66) | 5 | 0 | 4 | 4 | 4 | 4 |
| (67) | 2.5 | 0 | 5 | 4 | 4 | 4 |
| (69) | 1.25 | 0 | 4 | 4 | — | — |
| (70) | 5 | 0 | 4 | 4 | 4 | — |
| (73) | 2.5 | 1 | 5 | 5 | — | 4 |
| (74) | 5 | 1 | 5 | 5 | 4 | 4 |
| | 1.25 | 0 | 5 | 4 | — | 4 |
| (77) | 5 | 1 | 5 | 5 | 4 | 4 |
| | 1.25 | 1 | 5 | 5 | — | — |
| (B) | 20 | 2 | 4 | 4 | 4 | 1 |
| | 5 | 0 | 2 | 2 | 3 | 0 |
| (F) | 10 | 0 | 0 | 0 | 0 | 0 |
| | 2.5 | 0 | 0 | 0 | 0 | 0 |

Test Example 3 (Treatment for flooded paddy field)

Paddy field soil filled in a cylindrical plastic pot, 8 cm in diameter and 12 cm deep, was sown with barnyard grass. (The seeds were mixed with the soil in a depth of 1-2 cm.) After flooding, rice seedlings of 2-leaf stage were transplanted and grown in a greenhouse. Six days later (when weeds began to grow), a prescribed amount of sample granule prepared according to Formulation Example 3 was applied to the water after dilution with 5 ml of water. The plants were grown in a greenhouse for 20 days, and the herbicidal effect was observed. The results are shown in Table 6.

TABLE 6

| Sample compound | Dosage (g/acre) | Herbicidal Effect Rice | Barnyard grass |
|---|---|---|---|
| (1) | 40 | 1 | 5 |
|  | 10 | 1 | 4 |
| (5) | 40 | 0 | 4 |
| (7) | 40 | 1 | 5 |
|  | 10 | 1 | 4 |
| (9) | 40 | 1 | 5 |
| (10) | 40 | 1 | 5 |
|  | 10 | 1 | 4 |
| (12) | 40 | 1 | 5 |
|  | 10 | 1 | 5 |
| (13) | 40 | 1 | 5 |
| (A) | 40 | 4 | 1 |

Test Example 4 (Treatment for flooded paddy field)

Paddy field soil filled in a cylindrical plastic pot, 8 cm in diameter and 12 cm deep, was sown with barnyard grass. (The seeds were mixed with the soil in a depth of 1-2 cm.) After flooding, the weed was grown in a greenhouse. Six days later (when the weed began to grow), a prescribed amount of sample emulsion prepared according to Formulation Example 2 was applied to the water after dilution with 5 ml of water. The weed was grown in a greenhouse for 20 days, and the herbicidal effect was observed. The results are shown in Table 7.

TABLE 7

| Compound tested | Dosage (g/acre) | Herbicidal effect Barnyard grass |
|---|---|---|
| (2) | 40 | 5 |
| (4) | 40 | 5 |
| (5) | 40 | 4 |
| (7) | 40 | 5 |
| (9) | 40 | 5 |
| (10) | 40 | 5 |
| (12) | 40 | 5 |
| (24) | 40 | 4 |
| (25) | 40 | 4 |
| (26) | 40 | 5 |
| (27) | 40 | 5 |
| (28) | 40 | 5 |
| (29) | 40 | 5 |
| (30) | 40 | 5 |
| (31) | 40 | 5 |
| (33) | 40 | 4 |
| (35) | 40 | 5 |
| (36) | 40 | 4 |
| (38) | 40 | 5 |
| (42) | 40 | 5 |
| (45) | 40 | 4 |
| (49) | 40 | 4 |
| (50) | 40 | 4 |
| (51) | 40 | 5 |
| (54) | 40 | 5 |
| (57) | 40 | 4 |
| (65) | 40 | 5 |
| (66) | 40 | 5 |
| (67) | 40 | 5 |
| (69) | 40 | 5 |
| (70) | 40 | 5 |
| (74) | 40 | 5 |
| (76) | 40 | 4 |
| (77) | 40 | 4 |
| (78) | 40 | 5 |
| (80) | 40 | 5 |
| (83) | 40 | 5 |
| (86) | 40 | 5 |
| (88) | 40 | 5 |
| (89) | 40 | 4 |
| (90) | 40 | 4 |
| (92) | 40 | 5 |

TABLE 7-continued

| Compound tested | Dosage (g/acre) | Herbicidal effect Barnyard grass |
|---|---|---|
| (93) | 40 | 4 |

Test Example 5 (Treatment for flooded paddy field)

Paddy field soil filled in a 1/5000-a Wagner pot was sown with barnyard grass. (The seeds were mixed with the soil in a depth of 1-2 cm.) After flooding, rice seedlings of 3-leaf stage were transplanted and grown in a greenhouse. Six days later, a prescribed amount of sample granule prepared according to Formulation Example 3 was applied to the water. The rice and weed were grown in a greenhouse for 20 days, and the herbicidal effect was observed. The results are shown in Table 8.

TABLE 8

| Compound tested | Dosage (g/acre) | Herbicidal effect Rice | Barnyard grass |
|---|---|---|---|
| (35) | 20 | 2 | 5 |
|  | 5 | 2 | 5 |
| (38) | 20 | 2 | 5 |
|  | 5 | 2 | 5 |
| (C) | 20 | 3 | 4 |
|  | 5 | 0 | 0 |

What is claimed is:

1. A compound of the formula,

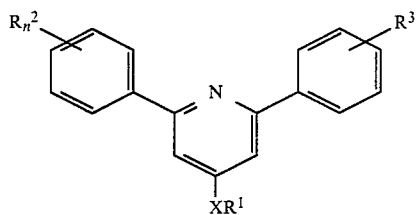

wherein $R^1$ is a $C_1$-$C_2$ alkyl group; $R^2$ is located at either the ortho or meta position and is selected from the group consisting of a halogen atom, methyl group and trifluoromethyl group; $R^3$ is a halogen atom, methyl group, or trifluoromethyl group; X is an oxygen or sulfur atom and n is equal to 0 or 1.

2. A compound according to claim 1, wherein $R^1$ is a $C_1$-$C_2$ alkyl group; $R^2$ is a halogen atom or trifluoromethyl group at the m-position; $R^3$ is a halogen atom or trifluoromethyl group at the p-position; and X is an oxygen or sulfur atom.

3. A compound according to claim 2, wherein R' is a methyl group, at least one of $R^2$ and $R^3$ is a trifluoromethyl group; and X is a sulfur atom.

4. A compound according to claim 3, of the formula,

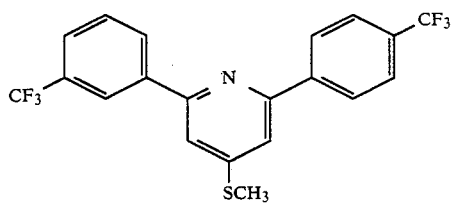

5. A herbicidal composition which comprises as an active ingredient a herbicidally effective amount of a compound of the following formula:

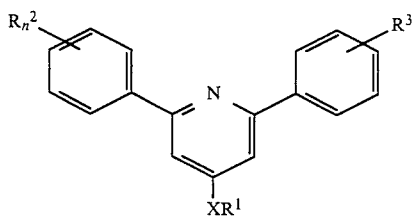

wherein $R^1$ is $C_1$–$C_2$ alkyl group; $R^2$ is located at either the ortho or meta position and is selected from the group consisting of a halogen atom, methyl group, and trifluoromethyl group; $R^3$ is a halogen atom, methyl group, or trifluoromethyl group; X is an oxygen or sulphur atom, n is equal to 0 or 1, and an inert carrier.

6. A method for controlling undesired weeds, which comprises applying a herbicidally effective amount of a compound of the following formula:

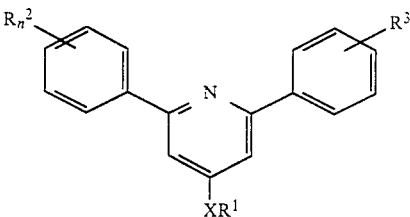

wherein $R^1$ is a $C_1$–$C_2$ alkyl group; $R^2$ is located at either the ortho or meta position and is selected from the group consisting of a halogen atom, methyl group and trifluoromethyl group; $R^3$ is a halogen atom, methyl group, or trifluoromethyl group; X is an oxygen or sulphur atom and n is equal to 0 or 1 and an inert carrier to an area where undesired weeds grow.

7. A method for controlling undesired weeds, which comprises applying a herbicidally effective amount of a compound of the following formula:

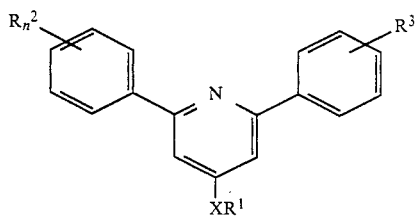

wherein $R^1$ is a $C_1$–$C_2$ alkyl group; $R^2$ is located at either the ortho or meta position and is selected from the group consisting of a halogen atom, methyl group and trifluoromethyl group; $R^3$ is a halogen atom, methyl group, or trifluoromethyl group; X is an oxygen or sulphur atom and n is equal to 0 or 1 and an inert carrier to a wheat or barley field.

* * * * *